United States Patent [19]
Simon et al.

[11] Patent Number: 5,147,628
[45] Date of Patent: Sep. 15, 1992

[54] PROCESS FOR PRODUCING ALKYLTETRAHYDROANTHRAHYDROQUINONES AND WORKING SOLUTIONS CONTAINING THEM FOR PRODUCING HYDROGEN PEROXIDE BY THE ANTHRAQUINONE PROCESS

[75] Inventors: Dietolf Simon; Otmar Woost, both of Bad Hoenningen, Fed. Rep. of Germany

[73] Assignee: Peroxid-Chemie GmbH, Hoellriegelskreuth, Fed. Rep. of Germany

[21] Appl. No.: 690,615

[22] Filed: Apr. 24, 1991

[30] Foreign Application Priority Data

Apr. 25, 1990 [DE] Fed. Rep. of Germany ....... 4013090

[51] Int. Cl.$^5$ .......................................... C01B 15/023
[52] U.S. Cl. .................................... 423/588; 552/208
[58] Field of Search ....................... 423/588; 552/208

[56] References Cited

U.S. PATENT DOCUMENTS

| 2,495,229 | 1/1950 | Dawsey et al. ............ 260/369 |
| 3,838,178 | 9/1974 | Graham . | |
| 3,888,890 | 6/1975 | Kirchner et al. . | |
| 4,374,820 | 2/1983 | Guenter ................. 423/588 |
| 4,514,376 | 4/1985 | Sethi .................... 423/588 |
| 4,539,196 | 9/1985 | Sethi et al. ............. 423/588 |
| 4,552,748 | 12/1985 | Berglin et al. . | |
| 4,783,284 | 11/1988 | Simon . | |
| 5,071,634 | 12/1991 | Maunula et al. ......... 423/588 |

FOREIGN PATENT DOCUMENTS

| 20042 | 7/1986 | Austria . |
| 40340 | 5/1989 | Austria . |
| 40341 | 5/1989 | Austria . |
| 70797 | 1/1983 | European Pat. Off. . |
| 216180 | 4/1987 | European Pat. Off. . |
| 2150390 | 10/1971 | Fed. Rep. of Germany . |
| 2331512 | 6/1973 | Fed. Rep. of Germany . |
| 3538816 | 5/1987 | Fed. Rep. of Germany . |

*Primary Examiner*—Wayne Langel
*Attorney, Agent, or Firm*—Foley & Lardner

[57] ABSTRACT

A process is disclosed for preparing alkyltetrahydroanthrahydroquinones in a solvent system suitable for the production of hydrogen peroxide. The resulting alkyltetrahydroanthrahydroquinone solutions can be used directly as working solutions for preparing $H_2O_2$ by the anthraquinone process. It is also possible, if desired, to isolate the alkyltetrahydroanthrahydroquinones from the solution, or to oxidize the alkyltetrahydroanthrahydroquinones with an oxygen-containing gas to the corresponding alkyltetrahydroanthraquinones, which can then be isolated.

14 Claims, No Drawings

PROCESS FOR PRODUCING ALKYLTETRAHYDROANTHRAHYDROQUINONES AND WORKING SOLUTIONS CONTAINING THEM FOR PRODUCING HYDROGEN PEROXIDE BY THE ANTHRAQUINONE PROCESS

BACKGROUND OF THE INVENTION

This invention relates to an improved process for producing alkyltetrahydroanthrahydroquinones in solvent systems suitable for the production of hydrogen peroxide, in which solutions of alkyl- 5,6,7,8-tetrahydroanthrahydroquinones are obtained which can be used directly as working solutions for the production of hydrogen peroxide, or from which alkyltetrahydroanthrahydroquinones or, following their oxidation with an oxygen-containing gas, the corresponding alkyltetrahydroanthraquinones can be isolated, if desired.

In the production of hydrogen peroxide by the anthraquinone process (AO process), alkylanthraquinones dissolved in suitable solvents are used as reaction carriers. These solutions of alkylanthraquinones are referred to as working solutions. It is also known that alkylanthraquinones in admixture with hydrogenation resistant alkyl-5,6,7,8-tetrahydroanthraquinones can be used in the working solution for the production of hydrogen peroxide by the anthraquinone process. The tetrahydroanthraquinones are formed spontaneously in succession during the process cycle as hydrogenation by-products of the alkylanthraquinones in the working solution. In order to be able to make better use of the advantages of alkyltetrahydroanthraquinones in the production of hydrogen peroxide, it is known in the art to produce the tetrahydro derivatives in separate syntheses and isolate them, so that they can be used directly in the AO process. It is also known from U.S. Pat. No. 4,514,376 that the proportion of tetrahydro derivatives relative to the alkylanthraquinones in the working solution of the AO process can be increased by adding a solution produced separately by hydrogenation (palladium, 50 to 400 kPa, temperature not greater than 50° C.) having an increased tetrahydro derivative content to a standard alkylanthraquinone working solution maximally in such an amount that the solubility of the tetrahydro derivative in the hydrogenation stage of the AO cyclic process is not exceeded. Although the foregoing process enables the production of hydrogen peroxide using working solutions with an improved ratio of alkyltetrahydroanthraquinone to alkylanthraquinone, it has not yet proved possible in the art to produce by a simple direct process working solutions which contain substantially only alkyltetrahydroanthraquinones as reaction carriers for producing hydrogen peroxide by the AO process.

SUMMARY OF THE INVENTION

It is the object of the present invention to provide a process which makes it possible to hydrogenate alkylanthraquinones to the corresponding tetrahydro compounds with a high yield and selectivity.

A further object of the invention is to provide a process which produces tetrahydro derivatives with sufficient yield and selectivity that the alkyltetrahydroanthrahydroquinone solutions obtained during this hydrogenation process can be used directly as working solutions for producing hydrogen peroxide by the AO process.

Another object of the invention is to provide a process which substantially eliminates drawbacks such as the formation of inhomogenous products.

These and other objects of the invention are achieved by providing a process for producing an alkyltetrahydroanthrahydroquinone product solution by heterogeneously catalyzed pressure hydrogenation of a an alkylanthraquinone starting solution, comprising reacting a solution of an alkylanthraquinone in a solvent system suitable for the production of hydrogen peroxide by the anthraquinone process under intensive mixing with hydrogen gas on a suspension catalyst or a carrier suspension catalyst selected from the group consisting of nickel, platinum and rhodium at a temperature in the range from 20° to 100° C. and a pressure of at least 400 kPa.

DETAILED DESCRIPTION OF PREFERRED EMBODIMENTS

As noted above, the invention relates to a process for producing solutions containing alkyltetrahydroanthrahydroquinone (product solutions) by heterogeneously catalyzed pressure hydrogenation of solutions containing alkylanthraquinone (starting solutions) in which a solution of alkylanthraquinone in a solvent system suitable for the production of hydrogen peroxide by the anthraquinone process is reacted under intensive mixing with hydrogen gas on a metallic suspension catalyst or carrier suspension catalyst selected from the group consisting of nickel, platinum or rhodium at temperatures from 20° to 100° C., preferably from 50° to 70° C., and at a pressure of at least 400 kPa, preferably from 800 to 1500 kPa.

This process is very simple to carry out and gives solutions of tetrahydro derivatives in the hydroquinone form (alkyltetrahydroanthrahydroquinones) in high yields and in a highly selective manner. In turn, the alkyltetrahydroanthrahydroquinones in these solutions can be converted in a known manner to the corresponding alkyltetrahydroanthraquinones by oxidation with an oxygen-containing gas. For this reason, the alkyltetrahydroanthrahydroquinone solutions produced according to the invention can advantageously be used as such directly in the anthraquinone process for synthesizing hydrogen peroxide, during which they are converted to alkyltetrahydroanthraquinone and $H_2O_2$. Of course, the alkyltetrahydroanthrahydroquinone containing solutions produced according to the invention are not suitable only for the production of hydrogen peroxide according to the AO process.

When the process according to the invention is carried out, the alkylanthraquinone to be hydrogenated is dissolved in a solvent or solvent system which is suitable as such for the production of working solutions for the AO process. In particular, solvent systems of two or more solvents are used which are equally suitable for the different dissolution properties of quinones and hydroquinones such as those occurring in the AO process. Mixtures of non-polar aromatic solvents (quinone solvents) and polar solvents (hydroquinone solvents) are therefore preferred for the process according to the invention. Examples of suitable aromatic solvents include alkyl-substituted aromatics, particularly $C_9$ and $C_{10}$ alkyl benzenes or mixtures thereof. Examples of suitable polar solvents include higher alcohols (e.g. diisobutylcarbinol or 2-octanol), alkylated and arylated urea, phosphoric acid esters (e.g. trioctyl phosphate), 2-pyrrolidone, 2-methylcyclohexyl acetate or mixtures thereof. Examples of suitable solvent mixtures include mixtures of $C_{10}$ alkyl aromatics with diisobutylcarbinol or with 2-methylcyclohexyl acetate.

The hydrogenation takes place on a suspension catalyst or carrier suspension catalyst of the metals nickel, platinum or rhodium, which is present in the heterogeneous form. In preferred embodiments of the process of the invention, the suspension catalyst may be Raney nickel or the carrier suspension catalyst may be platinum or rhodium metal on aluminum oxide, aluminum silicate, $SiO_2$, $TiO_2$ or carbon. In the case of carrier suspension catalysts, platinum or rhodium metal on aluminum silicate, $SiO_2$ or carbon is preferred. Raney nickel is particularly preferred as hydrogenation catalyst since it is superior to the noble metal carrier catalysts in terms of its rate of nucleus hydrogenation while having a good selectivity and, in addition, is far superior to the other catalysts even after economic considerations are taken into account.

According to the process of the invention, the concentration of the catalyst is preferably within a range which corresponds to a suspension density of the suspension or carrier suspension catalyst of 0.2 to 10% by wt. Preferably, the suspension density is 0.5 to 2.5% by wt.

Anthraquinones alkylated in the 2-position are desirably used as the alkyl-anthraquinones to be hydrogenated. It is particularly preferred to hydrogenate anthraquinones which are substituted in the C2 position by one $C_1$ to $C_{10}$ alkyl group, preferably by one $C_2$ to $C_5$ alkyl group. Suitable anthraquinones include 2-ethylanthraquinones, 2-butylanthraquinones, 2-amylanthraquinones or mixtures thereof. 2-ethylanthraquinone, 2-tertiary butylanthraquinone, 2-sec amylanthraquinone, 2-tertiary amylanthraquinone or mixtures thereof are particularly preferred.

According to an advantageous embodiment of the process of the invention, the starting solution contains from 2 to 20% by weight alkylanthraquinone or mixtures thereof (based on the total weight of the starting solution). Starting solutions containing from 5 to 15% by weight of the alkylanthraquinone or mixtures of alkylanthraquinones are particularly preferred.

Apart from intensive mixing of the hydrogenation mixture, the hydrogenation parameters of temperature and pressure are of particular importance for the success of the process according to the invention. The process according to the invention is carried out at elevated pressure, particularly at a pressure of more than 400 kPa, and at a temperature from 20° to 100° C. It is particularly preferred to carry out the hydrogenation at a hydrogen pressure of 800 to 1500 kPa. It is also particularly preferred for the temperature of the hydrogenation step to be within the range from 50° to 70° C. These latter particularly preferred pressures and temperatures produce the most advantageous relationships between the yield, the selectivity and the rate of conversion.

Compared to the in situ formation of alkyltetrahydroanthrahydroquinones during the production of $H_2O_2$ according to the AO process, the process of the invention has the advantage that, as a result of the nucleus hydrogenation of alkylanthraquinone outside to the AO process, a separate synthesis of alkyltetrahydroanthrahydroquinones can be carried out under optimum conditions, namely in the solvent system of the AO process. The hydrogenation reaction is completed within short periods, e.g. within a maximum of approximately 2 to 3 hours. According to a preferred variant of the process according to the invention, the hydrogenation can be completed in very short periods of approximately 20 minutes to 1 hour. The process according to the invention is also characterized by high yields. It is possible to carry out numerous hydrogenation cycles without noticeable deterioration of the catalyst activity, particularly when a Raney nickel catalyst is used. As a result of the high selectivity achieved, the formation of secondary products which could contaminate the end product (e.g. the alkyltetrahydroanthrahydroquinone working solution which is to be passed to the AO process) is kept to an absolute minimum. The product solution containing alkyltetrahydroanthrahydroquinone can—provided the same catalyst is used both for producing the product solution and for producing hydrogen peroxide according to the AO process—be passed directly to the hydrogenation stage of the AO process. If, on the other hand, a) different hydrogenation catalysts are used for the production of the working solution and for the AO process and/or b) the working solution produced is to be passed to the oxidation stage of the AO process, it is necessary to separate the hydrogenation catalyst from the working solution so as to avoid problems in case a) caused by undesirable mixing of different catalysts and in case b) caused by decomposition of hydrogen peroxide formed in the oxidation stage of the AO process. The catalyst may be separated from the product solution by known measures such as decanting, filtering, centrifuging, etc.

Moreover, after separating the catalyst from the product solutions produced according to the invention, the alkyltetrahydroanthrahydroquinones can be isolated from the product solution produced according to the invention—in particular for applications other than the production of $H_2O_2$ according to the AO process. If the quinone form (alkyltetrahydroanthraquinone) is desired rather than the alkyltetrahydroanthrahydroquinones themselves (i.e. the hydroquinone form of the product), it is possible, after the catalyst has been removed, to oxidize the hydroquinone form present in the product solution to the quinone form by reacting it with an oxygen-containing gas (e.g. air) and to subsequently isolate the resulting alkyltetrahydroanthraquinone—if necessary after separating any hydrogen peroxide which forms. The isolation of the alkyltetrahydroanthrahydroquinone or alkyltetrahydroanthraquinone can, for example, be of interest to the supplier of quinone to $H_2O_2$ plants, for transport reasons. For this reason, the invention also relates to a process for the production of alkyltetrahydroanthrahydroquinone or alkyltetrahydroanthraquinone which is characterized in that, according to the process of the invention described above, a catalyst-free solution containing alkyltetrahydroanthrahydroquinone (catalyst-free product solution) is first produced by the heterogeneously catalyzed pressure hydrogenation of solutions containing alkylanthraquinone (starting solution) and subsequent separation of the catalyst and that thereafter either a) the alkyltetrahydroanthraquinone is isolated from the catalyst-free product solution or b) the alkyltetrahydroanthrahydroquinone contained in the catalyst-free product solution is oxidized by conversion with an oxygen-containing gas and the alkyltetrahydroanthraquinone thus formed is isolated. The products are isolated by known measures, e.g. by cooling the solution containing the products and subsequent filtration or centrifuging etc. of the resulting precipitate. On the other hand, the products can also be obtained by distilling off the solvent. Because of the high rate of hydrogenation, and the high selectivity of hydrogenation the solid products are obtained in a high yield simultaneously with a high purity.

It is not necessary to isolate the alkyltetrahydroanthrahydroquinones in order to use them for the production of hydrogen peroxide according to the AO process, their isolation from the product solution is not necessary. The alkyltetrahydroanthrahydroquinone formed according to the invention is advantageously present in such a concentration and purity in a solvent or solvent system suitable for the $H_2O_2$ synthesis according to the AO process that the solutions produced according to the process described above can be transferred directly, i.e. without further purification or reconcentration, into the AO process for the production of $H_2O_2$.

The invention therefore relates also to a process for producing hydrogen peroxide by the anthraquinone process during which a working solution is passed in a known manner cyclically through an operating cycle consisting of a hydrogenation stage, an oxidation stage and an extraction stage and which is characterized in that a working solution is used as reaction carrier which essentially contains only alkyltetrahydroanthrahydroquinone and which is initially produced in a hydrogenation stage separate from the operating cycle by the heterogeneously catalyzed pressure hydrogenation of a solution containing alkylanthraquinone by reacting a solution of alkylanthraquinone in a solvent system suitable for the production of hydrogen peroxide by the anthraquinone process under intensive mixing with hydrogen gas on a suspension catalyst or carrier suspension catalyst of the metals nickel, platinum or rhodium at temperatures from 20° to 100° C., preferably from 50° to 70° C., and at a pressure of at least 400 kPa, preferably from 800 to 1500 kPa, and which, optionally after separating the suspension or carrier suspension catalyst, is passed to the operating cycle of the AO process (taking the measures described above into account).

The advantages of this process for preparing $H_2O_2$ by the AO process result directly from the advantages of the alkyltetrahydroanthrahydroquinone solution used, which is obtained by the process for producing alkyltetrahydroanthrahydroquinone working solutions according to the invention as described above. The high yield, selectivity and purity and the short hydrogenation times in the process according to the invention for producing alkyltetrahydroanthrahydroquinone solutions in a solvent or solvent mixture suitable for the AO process, allow a high measure of flexibility during the production of $H_2O_2$ by the AO process, as a result of which substantial short-term productivity increases can be achieved.

The invention is illustrated in further detail by the following examples which are merely illustrative and do not limit the scope of the invention.

EXAMPLES

The following examples were carried out in a loop-type hydrogenation reactor, the design and basic operating principles of which are described in further detail, e.g. in European patent application No. EP 70,797 and which, because of its high mixing efficiency, effectively assures the desired intensive mixing of the hydrogenation preparation in the process of the invention.

The reaction material (solution of alkylanthraquinones and catalyst), whose composition is indicated in Table 1, was first introduced into a container and the heterogeneous mixture was then transferred into the reaction loop of the reactor. The main parts of the reaction loop were: an autoclave used as the actual reaction vessel having an injector mixing nozzle passing into the top of the vessel and having an opening in the bottom of the reaction vessel as well as further inlets and outlets for the reaction material or the product solution; a rotary pump; a heat exchanger; a gas feed line to the injector mixing nozzle, and a loop line. The loop line connected the aforementioned parts of the reactor in the following sequence: bottom of the reaction vessel, rotary pump, heat exchanger, and injector mixing nozzle, in order to form the so-called reaction loop.

During the hydrogenation, the reaction material was pumped continuously through the reaction loop while hydrogen was mixed in homogeneously according to the injector principle in the injector mixing nozzle. In the injector mixing nozzle, the hydrogenation gas and the reaction material were mixed intensively, and, as a result of the high shearing forces produced in the nozzle, the hydrogenation was advantageously promoted under the conditions according to the invention, so that the alkylanthraquinones could be converted to alkyltetrahydroanthrahydroquinones with high yields and selectivities as well as a greatly increased rate of hydrogenation.

The hydrogenation of 45 kg reaction material in each case was carried out by varying the catalyst, the alkylanthraquinone, the alkylanthraquinone concentration, the temperature, the pressure, the solvent and the reaction time. Table 1 provides a summary of the results obtained.

TABLE 1

| Ex. No. | Starting Solution (concentration of g/kg soln.) | | Catalyst & Susp. Density (%) | Temp. (°C.) | Pressure (kPa) | Reaction Time (min) | Hydrogenation conversion (%)*** | Selectivity of tetrahydro cpd. formation (%)**** |
|---|---|---|---|---|---|---|---|---|
| | Anthraquinone alkyl-group* | Solvent Mixture | | | | | | |
| 1 | 2-amyl (100) | diisobutylcarbinol (270)/$C_{10}$ alkyl-aromatic mixture (630) | Raney Nickel (1.0) | 50 | 800 | 110 | 96.1 | 94.5 |
| 2 | same as Ex. 1 | same as Ex. 1 | as Ex. 1 | 70 | 1500 | 22 | 96.4 | 95.0 |
| 3 | same as Ex. 1 | same as Ex. 1 | as Ex. 1 | 70 | 800 | 24 | 92.2 | 93.2 |
| 4 | same as Ex. 1 | same as Ex. 1 | as Ex. 1 | 50 | 1500 | 50 | 93.5 | 97.0 |
| 5 | 2-amyl (70) 2-ethyl (30)** | same as Ex. 1 | as Ex. 1 | 70 | 1500 | 17 | 93.0 | 96.3 |
| 6 | 2-ethyl (50) | 2-methylcyclohexyl acetate (390)/$C_{10}$ alkyl | as Ex. 1 | 70 | 1500 | 27 | 93.7 | 97.9 |

TABLE 1-continued

| Ex. No. | Starting Solution (concentration of g/kg soln.) Anthraquinone alkyl-group* | Solvent Mixture | Catalyst & Susp. Density (%) | Temp. (°C.) | Pressure (kPa) | Reaction Time (min) | Hydrogenation conversion (%)*** | Selectivity of tetra-hydro cpd. formation (%)**** |
|---|---|---|---|---|---|---|---|---|
| 7 | 2-amyl (100) | aromatic mix. (560) diisobutylcarbinol (300)/$C_{10}$ alkyl-aromatic mixture (600) | 2% Pt on $Al_xSiO_y$ carrier (0.8) | 70 | 800 | 170 | 84.0 | 93.9 |
| 8 | same as Ex. 7 | same as Ex. 7 | as Ex. 7 except (2.2) | 70 | 1200 | 30 | 99.3 | 99 |

*2-amylanthraquinone = isomer mixture of secondary and tertiary amylanthraquinone
**Mixture of 2-amylanthraquinone and 2-ethylanthraquinone
***Based on amount of alkylanthraquinone used
****Amount of tetrahydro derivative formed based on the amount of alkylanthraquinone used With respect to Example 2, it should be mentioned that the Raney nickel catalyst used could be reused in six consecutive operations without any significant decrease in the activity of the catalyst occurring during the subsequent hydrogenation processes. After separating the suspended catalyst, the solutions obtained in the reactions of the above-mentioned examples could be passed to a production cycle for producing hydrogen peroxide by the anthraquinone process. However, if the same catalysts used for producing the alkyltetrahydroanthrahydroquinone working solutions were also used in the AO process for producing $H_2O_2$ then the working solutions could be passed directly to the AO process operating cycle without separating the catalyst. The production of hydrogen peroxide using working solutions of alkyltetrahydroanthrahydroquinone produced according to the process of the invention, can be carried out with particular advantage as regards the hydrogenation stability of the reactants alkyltetrahydroanthrahydroquinone/anthraquinone. In other words, the formation of undesirable hydrogenation by-products in the AO hydrogenation stage was largely avoided, as a result of which the consumption of quinone was reduced and quinone could be conserved.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A process for producing an alkyltetrahydroanthrahydroquinone product solution by heterogeneously catalyzed pressure hydrogenation of an alkylanthraquinone starting solution in a loop-type hydrogenation reactor equipped with an injector mixing nozzle, comprising hydrogenating a solution of alkylanthraquinone in a solvent system suitable for the production of hydrogen peroxide by the anthraquinone process in the presence of a suspension catalyst or a carrier suspension catalyst selected from the group consisting of nickel, platinum and rhodium at a temperature in the range from 50° to 75° C. and a pressure in the range from 800 to 1500 kPa, by continuously pumping the anthraquinone solution through the reactor loop while hydrogen gas is homogeneously introduced into the solution with intensive mixing through the injector mixing nozzle.

2. A process according to claim 1, wherein said catalyst is a Raney Nickel suspension catalyst or a platinum or rhodium metal carrier suspension catalyst on a carrier selected from the group consisting of aluminum oxide, aluminum silicate, $SiO_2$, $TiO_2$ and carbon.

3. A process according to claim 2, wherein said catalyst is a platinum or rhodium metal carrier suspension catalyst on a carrier selected from the group consisting of aluminum silicate, $SiO_2$ and carbon.

4. A process according to claim 1, wherein said suspension or carrier suspension catalyst has a suspension density in the range from 0.2 to 10% by weight.

5. A process according to claim 4, wherein said catalyst has a suspension density in the range from 0.5 to 2.5% by weight.

6. A process according to claim 1, wherein said alkylanthraquinone is an alkylanthraquinone substituted in the C2 position by a $C_1$ to $C_{10}$ alkyl group.

7. A process according to claim 6, wherein said alkylanthraquinone is an alkylanthraquinone substituted in the C2 position by a $C_2$ to $C_5$ alkyl group.

8. A process according to claim 6, wherein said alkylanthraquinone is selected from the group consisting of 2-ethylanthraquinone, 2-butylanthraquinone, 2-amylanthraquinone and mixtures thereof.

9. A process according to claim 8, wherein said alkylanthraquinone is selected from the group consisting of 2-ethylanthraquinone, 2-tertiary butylanthraquinone, 2-sec amylanthraquinone 2-tertiary amylanthraquinone and mixtures thereof.

10. A process according to claim 1, wherein said starting solution contains from 2 to 20% by weight alkylanthraquinone based on the total weight of the starting solution.

11. A process according to claim 10, wherein said starting solution contains from 5 to 15% by weight alkylanthraquinone based on the total weight of the starting solution.

12. A process according to claim 1, for producing alkyltetrahydroanthrahydroquinone or alkyltetrahydroanthraquinone comprising subjecting an anthraquinone starting solution to heterogeneously catalyzed pressure hydrogenation to produce an alkyltetrahydroanthrahydroquinone product solution and subsequently separating the catalyst to produce a catalyst-free product solution, and (a) if an alkyltetrahydroanthrahydroquinone is to be produced, isolating the alkyltetrahydroanthrahydroquinone from the catalyst-free product solution, or (b) if an alkyltetrahydroanthrahydroquinone is to be produced, oxidizing the alkyltetrahydroanthrahydroquinone contained in the catalyst-free product solution to the corresponding alkyltetrahydroanthrahydroquinone by reacting it with an oxygen-containing gas, and thereafter isolating the resulting alkyltetrahydroanthrahydroquinone.

13. A process for preparing hydrogen peroxide comprising the steps of initially producing a working solution consisting essentially of alkyltetrahydroanthrahydroquinone in a solvent system suitable for the production of hydrogen peroxide by the anthraquinone process, said working solution being produced by heterogeneously catalyzed pressure hydrogenation of an alkylanthraquinone solution in said solvent system in a separate initial hydrogenation stage in a loop-type hydrogenation reactor equipped with an injector mixing nozzle, by hydrogenating a solution of alkylanthraquinone in the presence of a suspension catalyst or carrier suspension catalyst selected from the group consisting of nickel, platinum and rhodium at a temperature in the range from 50° to 70° C. and at a pressure in the range from 800 to 1500 kPa, by continuously pumping the anthraquinone solution through the reactor loop while hydrogen gas is homogeneously introduced into the solution with intensive mixing through the injector mixing nozzle, and subsequently passing said working solution cyclically through an anthraquinone process operating cycle comprising an anthraquinone cycle hydrogenation stage, an oxidation stage and an extraction stage, to produce $H_2O_2$.

14. A process according to claim 13, further comprising separating said suspension or carrier suspension catalyst from said working solution prior to passing said working solution to said operating cycle.

* * * * *